(12) United States Patent
Golovashchenko

(10) Patent No.: US 8,511,178 B2
(45) Date of Patent: Aug. 20, 2013

(54) SCREENING TEST FOR STRETCH FLANGING A TRIMMED METAL SURFACE

(75) Inventor: Sergey Fedorovich Golovashchenko, Beverly Hills, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 228 days.

(21) Appl. No.: 13/078,509

(22) Filed: Apr. 1, 2011

(65) Prior Publication Data
US 2012/0247222 A1  Oct. 4, 2012

(51) Int. Cl.
*G01N 3/20* (2006.01)
(52) U.S. Cl.
USPC ................................. 73/849; 73/856
(58) Field of Classification Search
USPC .......................... 73/760, 849, 856
See application file for complete search history.

(56) References Cited

U.S. PATENT DOCUMENTS

| | | | |
|---|---|---|---|
| 2,742,782 A * | 4/1956 | Mironoff | 73/853 |
| 4,358,962 A * | 11/1982 | Ashby et al. | 73/849 |
| 4,566,335 A * | 1/1986 | Singhal | 73/849 |
| 5,187,987 A * | 2/1993 | Anderson et al. | 73/852 |
| 5,199,305 A * | 4/1993 | Smith et al. | 73/851 |
| 5,277,069 A * | 1/1994 | Cussac et al. | 73/853 |
| 5,507,189 A | 4/1996 | Kim et al. | |
| 6,522,979 B1 | 2/2003 | Yavari et al. | |
| 7,143,658 B2 * | 12/2006 | Schubert | 73/862.632 |
| 7,156,930 B2 * | 1/2007 | Kashiwazaki et al. | 148/440 |
| 7,185,521 B2 * | 3/2007 | Lombardo et al. | 72/75 |
| 7,424,832 B1 * | 9/2008 | Nunnelee | 73/862.472 |

FOREIGN PATENT DOCUMENTS
JP  2009145138 A  7/2009

OTHER PUBLICATIONS

JMEPEG, ASM International, Sergey F. Golovashchenko, Quality of Trimming and its Effect on Stretch Flanging of Automotive Panels, Submitted Oct. 26, 2007, in revised form Jan. 26, 2008.
Science Direct, Elsevier, Sergey F. Golovashchenko, A study on trimming of aluminum autobody sheet and development of a new robust process eliminating burrs and slivers, revised Aug. 23, 2004, received in revised form Jul. 12, 2006; accepted Jul. 12, 2006, available online Aug. 28, 2006.
Pergamon, Ming Li, International Journal of Mechanical Sciences, An experimental investigation on cut surface and burr in trimming aluminum autobody sheet, received in revised form Jan. 27, 1999.
Sergey F. Golovashchenko, ASM International, Analysis of Trimming of Aluminum Closure Panels, JMEPEG, Submitted Feb. 27, 2006; in revised form Jul. 2, 2006.

(Continued)

*Primary Examiner* — Max Noori
(74) *Attorney, Agent, or Firm* — Damian Porcari Brooks Kushman P.C.

(57) ABSTRACT

A method of testing metal samples is provided to simulate stretch flanging of trimmed surfaces. A sample having planar sides and a sidewall extending between the planar sides is placed in a fixture so that the planar sides are confined. The sidewall of the sample is bent about a curved surface while restricting buckling out of a planar area. One testing machine is disclosed in which a test specimen is clamped in a die with a nesting slot while a punch bends a sample against a forming surface that has a radius. In another testing machine, a mandrel and clamping element engage the planar sides of the sample while first and second bending members engage first and second end portions to bend one of the sidewalls of the sample about the mandrel.

4 Claims, 3 Drawing Sheets

(56) References Cited

OTHER PUBLICATIONS

American Association State Highway and Transportation, ASTM International, Designation E8/E8M-09, Standard Test Methods for Tension Testing of Metallic Materials.
R.G. Davies, Edge Cracking in High Strength Steels, Applied Metalworking, 1983 American Society for Metals, vol. 2, No. 4, Jan. 1983.
R. Narayanasamy, et al., Effect of mechanical and fractographic properties on hole expandability of various automobile steels during hole expansion test, Accepted 2009, Published online: Jul. 23, 2009.
D. I. Hyun, et al. Elsevier, Journal of Materials Processing Technology, 130-131 (2002) 9-13, Estimation of hole flangeability for high strength steel plates.
B.S. Levy and C.J. Van Tyne, Failure During Sheared Edge Stretching, submitted Jan. 29, 2008, JMEPEG, ASM International.
Daw-Kwei Leu, Pergamon, Int. J. Mech. Science, vol. 38, Nos. 8-9, pp. 917-933, Finite-Element Simulation of Hole-Flanging Process of Circular Sheets of Anisotropic Materials; and in revised form 5 Sep. 1995.
R.J. Comstock, Jr., et al., Hole Expansion in a Variety of Sheet Steels, ASM International, submitted Jan. 20, 2006.
You-Min Huang, et al. Journal of Materials Processing Technology, Influence of the punch profile on the limitation of formability in the hold-flanging process, (2001).

International Standard, ISO 16630, Reference No. 16630-2009(E), Metallic materials—sheet and strip—Hole expanding test, 2009, Feb. 10, 2010, Ford Motor Company.
Ming Li, International Journal of Mechanical Sciences 42 (2000), 907-923, Micromechanisms of deformation and fracture in shearing aluminum alloy sheet, received in revised form Jan. 27, 1999.
A. Konieczny and T. Henderson, SAE Technical Paper Series, 2007-01-0340, On formability Limitations in Stamping Involving Sheared Edge Stretching, Apr. 16-19, 2007.
Ming F. Shi and Xiaoming Chen, SAE Technical Paper Series, Prediction of Stretch Flangeability Limits of Advanced High Strength Steels Using the Hole Expansion Test, Apr. 16-19, 2007.
SAE Technical Paper Series, 2006-01-1589, J. Chintamani and S. Sriram, Sheared Edge Characterization of Steel products used for Closure Panel Applications, Apr. 3-6, 2006.
R.D. Adamczyk and G. M. Michal, Sheared Edge Extension of High Strength Cold Rolled Steels, vol. 4, No. 2, Jan. 1986.
Peter Dewhurst, Stretch Forming of Sheet Metal: a Mechanism of Deformation Involving Diffuse Neck Interaction.
Ching-Lun Li, et al., The analysis of forming limit in re-penetration process of the hole-flanging of sheet metal, (2008), 256-2160.
Ronald D. Adamczyk, et al., The Edge Formability of High-Strength Cold-Rolled Steel, 830237, Republic Steel Corp—Research Center, Independence, OH.
You-Min Huang, et al., The formability limitation of the hole-flanging process, Journal of Materials Processing Technology 117 (2001), 43-51.

* cited by examiner

SCREENING TEST FOR STRETCH FLANGING A TRIMMED METAL SURFACE

TECHNICAL FIELD

The present invention relates to a testing method for determining the performance of metal sample in a stretch flanging after trimming operation.

BACKGROUND

In sheet metal stamping operations on materials having reduced ductility, such as advance high strength steels, dual phase steel and aluminum alloys, one issue is that trimmed surfaces tend to split when they are formed into a flange. When a flange is formed on a contoured trimmed surface, the flange is stretched. Current testing methods have proven unreliable in predicting the formability of materials in stretch flanging operations.

In the prior art, a hole expansion test has been used to predict formability. In the hole expansion test, a small diameter hole is formed in a sheet metal blank and then a larger diameter punch is driven through the smaller diameter hole to form flanges. The larger diameter punch is driven through the smaller diameter hole until a through thickness crack appears on the edge of the hole. A limiting hole expansion ratio is calculated based upon the original hole diameter and the expanded hole diameter. Alternatively, a limiting forming ratio may be determined as the ratio of the expanded hole diameter to the original hole diameter.

Tensile testing of a sheared edge may be conducted on sample strips. Samples are trimmed to have a dog bone shape, half dog bone shape or straight sides. The samples are stretched in a direction parallel to the trimming line until failure.

A high degree of correlation is not generally exhibited between the tensile test and the hole expansion test. The expansion test and tensile test methodologies do not provide reliable data on the ability of a particular material specimen to stretch in a specific direction across the width of the flange in a flanging operation. Stretching the flange in the flanging operation may cause significant strain localization in a fracture zone.

Applicant's proposed test methodology has been developed to provide more reliable predictions of metal sample performance in a stretch forming operation that is performed after drawing and trimming operations.

SUMMARY

In the proposed testing method, a sample strip of sheet material is bent in the plane of the strip about a radius that is a function of the stretch flanging radius and height of the flange to be formed in the flanging operation to be simulated. Out of plane bending of the strip is prevented by supporting both planar sides of the strip during the bending operation. Applicant's methodology can be applied to stretch flanging or stretch hemming operations and provide reliable data for predicting the performance of a sample in a stretch flanging operation.

The test sequence may include the following steps:
pre-stretching the sheet metal to simulate the strain applied to the metal in a preceding draw operation;
trimming strip samples to simulate conditions in a production tool;
marking the sample with a grid or series of marks at a known regular small interval;
bending the strip in plane with the trimmed edge corresponding to the edge undergoing maximum stretching;
measuring the distance between the interval markings near the fracture area to compare the measurements with analytical calculations and finite element measurement results;
repeating the test on samples cut in the longitudinal, transverse and 45° to determine the effect of sample orientation.

The proposed test method may be used to provide a quick screening test in production stamping plants, especially where advanced high strength steels, dual phase steels and aluminum alloys are formed. The screening test can detect material property variation quickly before placing a coil or stack of material into production. By being better able to simulate the stretch flanging and stretch hemming stresses in the material, materials that lack desired properties or suffer from variation can be avoided. It may also be possible to provide a material specification that more closely predicts production performance. In addition, blank orientation may be optimized to prevent splits in stretch flanging and stretch hemming operations by aligning the stretch flanging direction with the direction of maximum formability for the trimmed surface.

According to one aspect of the disclosure, a method of testing metal for a flanging operation includes providing a sample of metal having planar sides and a sidewall that extends between the planar sides. The planar sides of the sample are confined in a fixture to a planar area. The sidewalls of the sample are then bent about a curved surface while restricting buckling out of the planar area.

According to other aspects of the method, the sample may be positioned in the confining step with the length of the sample being centered relative to the curved surface. A first lengthwise end and a second lengthwise end of the sample are engaged in the bending step to move the first and second ends to bend the sample about the curved surface. The curved surface preferably has a test radius that is a function of the stretch flanging radius and height of the flange to be formed in the flanging operation.

According to other aspects of the disclosure, the step of confining the planar side of the sample may include clamping a first lengthwise end of the sample with two opposed side edges of the sidewall being clamped between a clamping member and a die that define a slot. The slot is slightly larger than the width of the sample so that the planar sides of the sample are restrained, but not clamped within the slot. The step of bending the sidewall of the sample may include engaging a second lengthwise end of the sample on one of the opposed side edges of the sidewall with a punch that bends the sample about a curved surface.

Alternatively, the method disclosed may include the step of confining the planar sides of the sample by clamping a central portion of the planar sides of the sample with a portion of the sidewall adjacent to a mandrel. The central portion of the sample may be disposed between two spacing elements with first and second lengthwise ends of the sample extending from the spacing elements. The step of bending the sidewall of the sample may then include engaging the first and second lengthwise ends of the sample and moving both of the ends relative to the central portion.

According to other aspects of the disclosure, a test machine is disclosed for testing the elongated planar metal sample for suitability for use in a flanging operation in which a flange is stretched while the flange is formed. The test machine may include a die that has a forming surface and a clamping member that cooperates with the die to clamp a first longitudinal end of the sample. The die and clamping member engage two opposed portions of a sidewall of the sample and may also define a nesting slot that confines the planar sides of the sample. A punch engages a third portion of the sidewall on the opposite end of the forming surface from the two opposed portions to bend the sample against the forming surface. The sidewall engaged by the clamping member is stretched while the punch bends the sidewall of the sample against the forming surface.

The forming surface may have a radius that is a function of the stretch flanging radius and height of the flange to be formed in the flanging operation. The nesting slot may be defined by the die, the clamping member or by the combination of die and the clamping member. A clearance space may be defined between each of the planar sides of the sample and the nesting slot.

An alternative embodiment of the test machine is also disclosed for testing an elongated planar metal sample for suitability for use in a flanging operation in which a flange is stretched while the flange is formed. The alternative embodiment of the test machine includes a mandrel and first and second clamping elements that engage opposite planar sides of the sample. The clamping elements engage an intermediate portion of the sample that is secured with the sidewall against the mandrel. First and second bending members engage end portions of the sidewall of the sample on opposite ends of the intermediate portion of the sample to bend the sample about the mandrel. The sidewall between the first end portion and the second end portion is stretched while the first and second bending members bend the sample.

Additional aspects relating to the alternative embodiment of the test machine may include providing a mandrel with the first and second clamping elements comprising a plurality of washers assembled to the mandrel. The mandrel may then be secured to a fixture that retains the mandrel in a fixed location while the bending member bends the sample about the mandrel. The bending member may be clamps, a press apparatus, or a manual force that bends the sample around the mandrel.

According to another aspect of the disclosure, the sample may be cut from a quantity of material that is to be used in the flanging operation. The above aspects and features of the disclosure will be better understood in view of the attached drawings and the following detailed description of the illustrated embodiments.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
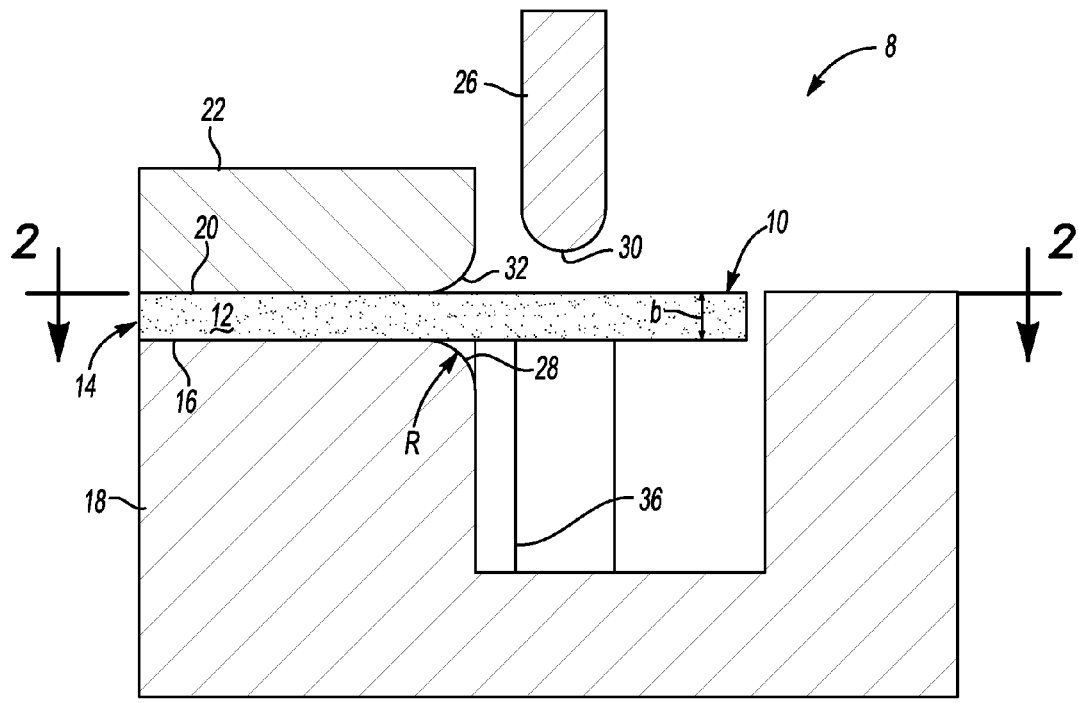
FIG. 1 is a diagrammatic cross-sectional view of a test machine with a sample retained in the machine prior to testing according to one embodiment of the present invention.

Referring to FIG. 1, a test machine 8 is shown with a test strip sample 10 loaded into the test machine 8 for testing. A first planar side 12 of the test strip sample 10 is shown to have a width b. The test strip sample 10 has a sidewall 14 that extends about the sample 10 between the first planar side 12 and a second planar side (not shown in FIG. 1). A first portion 16 of the sidewall 14 is supported on a die 18. A second portion 20 of the sidewall 14 is engaged by a clamp 22 that holds the test strip sample 10 in place during the test procedure. A punch 26 is driven into contact with the test strip sample 10 to form the test strip sample 10 about a forming surface 28 that has a radius. The forming surface 28 has a radius R that may either be a standard radius or a radius selected to correspond to a function of the stretch flanging radius and the height of the flange to be formed in the stretch flanging operation.

A relief radius 30 may be formed on the punch 26. Another relief radius 32 may be formed on the clamp 22. The relief radii 30, 32 are intended to reduce any tendency of the punch 26 or clamp 22 from tearing the test strip sample 10 during the testing procedure.

Figure 2:
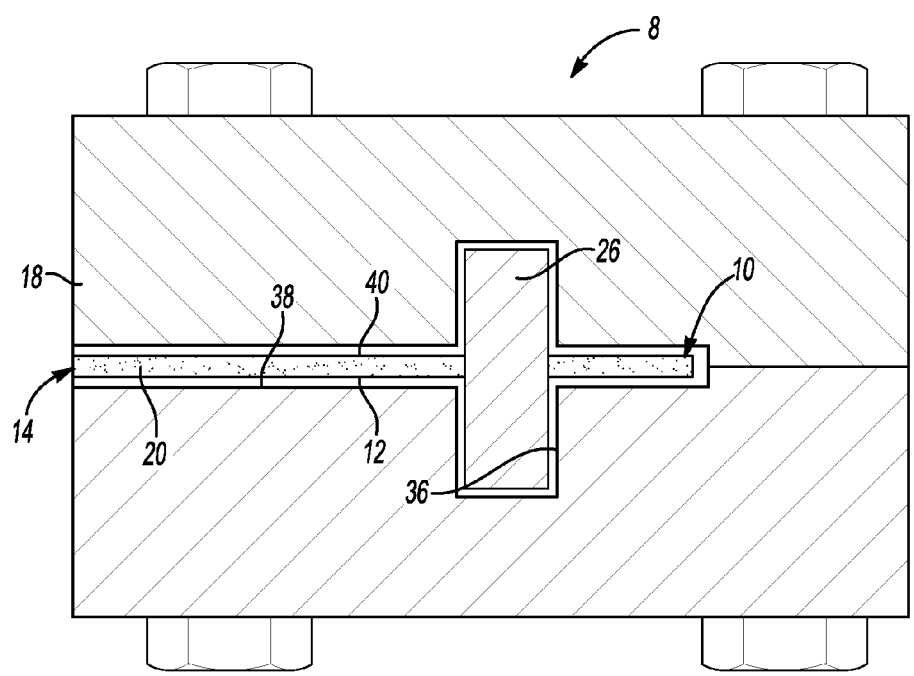
FIG. 2 is a diagrammatic cross-sectional view taken along the line 2-2 in FIG. 1.

Referring to FIGS. 1 and 2, a punch clearance slot 36 is provided to receive the punch 26. The test strip sample 10 is received in a nesting slot 38 that is provided to confine the first planar side 12 and a second planar sidewall 40 during the test procedure. In the test procedure, the punch 26 is driven into engagement with the test strip sample 10 and moved through the punch clearance slot 36 while the punch 26 bends the test strip sample 10 over the forming surface 28.

The test machine 8 is shown with the test strip sample 10 prior to bending. The first planar side 12 and second planar side 40 of the test strip sample 10 are shown with an exaggerated clearance between the test strip sample and the nesting slot 38. A second portion 20 of the sidewall 14 is visible in FIG. 2 that is engaged by the clamp 22 shown in FIG. 1. The die 18 defines the nesting slot 38, but it should be understood that the nesting slot could also be provided in the clamp 22 or partially in the clamp 22 and the die 18. The punch 26 is shown disposed above the punch clearance slot 36.

Figure 3:
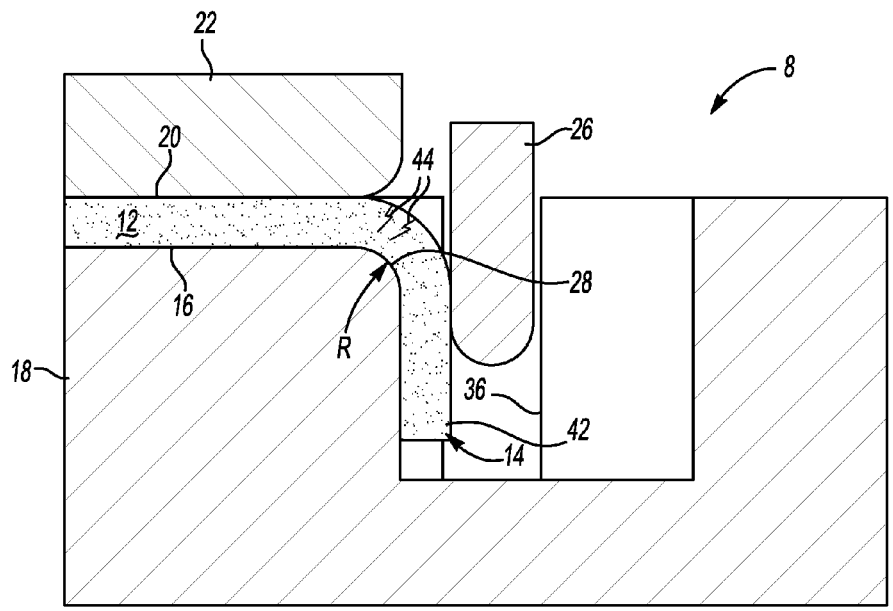
FIG. 3 is a diagrammatic elevation cross-sectional view of the test machine shown in FIG. 1 after the test sample is bent over a forming surface that has a radius.

Referring to FIG. 3, the test machine 8 is shown to include the die 18 and the clamp 22. The test strip 10 is partially retained on the first portion of the sidewall 16, while a second portion of the sidewall 20 is engaged by the clamp 22. In FIG. 3, the punch 26 is shown after engaging the test strip sample 10 (shown in FIGS. 1 and 2). A bent sample 42 is formed after the test strip sample 10 is bent about the forming surface 28. Fractures 44 may or may not be formed in the bent sample 42 depending upon the formability of the bent sample 42 after the simulated stretch flanging operation test. Fractures 44 tend to form in the part of the sidewall 14 that is opposite the portion of the sidewall 14 that engages the forming surface 28.

Figure 4:
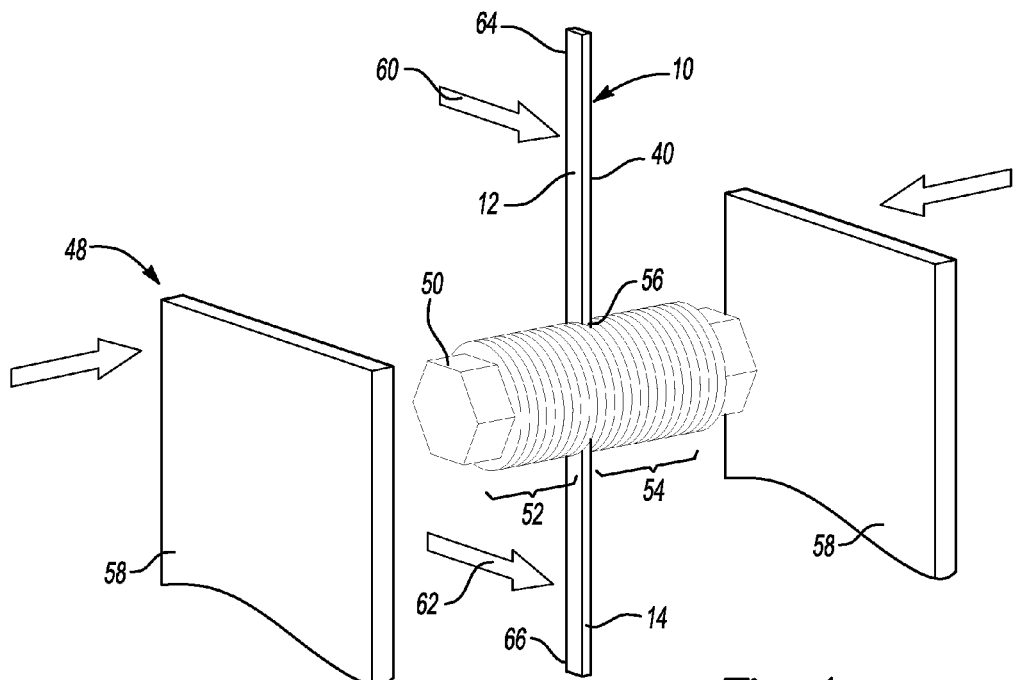
FIG. 4 is a partially exploded diagrammatic perspective view of an alternative embodiment of a test machine with a test sample loaded prior to testing.

Referring to FIG. 4, an alternative embodiment of a test machine 48 is shown to include a mandrel 50. The mandrel 50 may be a bolt, as illustrated, or may take another form. A first clamping element 52 is shown as a plurality of washers, but could take an alternative form, such as a cylindrical spacer. A second clamping element 54 is also shown as a plurality of washers. An intermediate portion 56 of a test strip sample 10 is clamped between the first and second clamping elements 52 and 54. The mandrel 50 is supported in a fixture 58 that may be a vice or other type of fixture capable of holding the mandrel 50 in place while the test strip sample 10 is bent about the mandrel 50. A first bending member 60 and a second bending member 62 are shown diagrammatically by arrows in FIG. 4. The bending members 60, 62 could be a pair of pliers or a fixture ram that exerts equal pressure on a first end portion 64 and a second end portion 68 of test strip sample 10.

Figure 5:
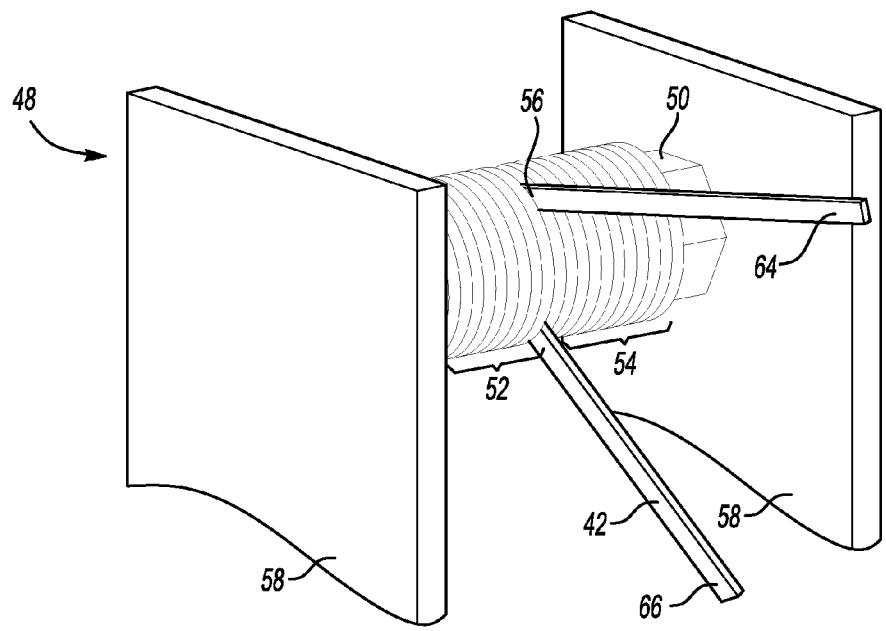
FIG. 5 is a fragmentary diagrammatic perspective view of the embodiment of the test machine shown in FIG. 4 after completion of the bending operation.

Referring to FIG. 5, the test machine 48 is shown with a bent sample 42 after the bending test has been performed. The mandrel 50 is retained by the fixture 58 and the bent sample 42 is retained between the first clamping element 52 and the second clamping element 54. The intermediate portion 56 of the bent sample 42 is bent by the force applied by the first bending member 60 and second bending member 62, as shown in FIG. 4. The first end portion 64 and second end portion 66 of the bent sample 42 are shown while they are bent during the test procedure.

Figure 6:
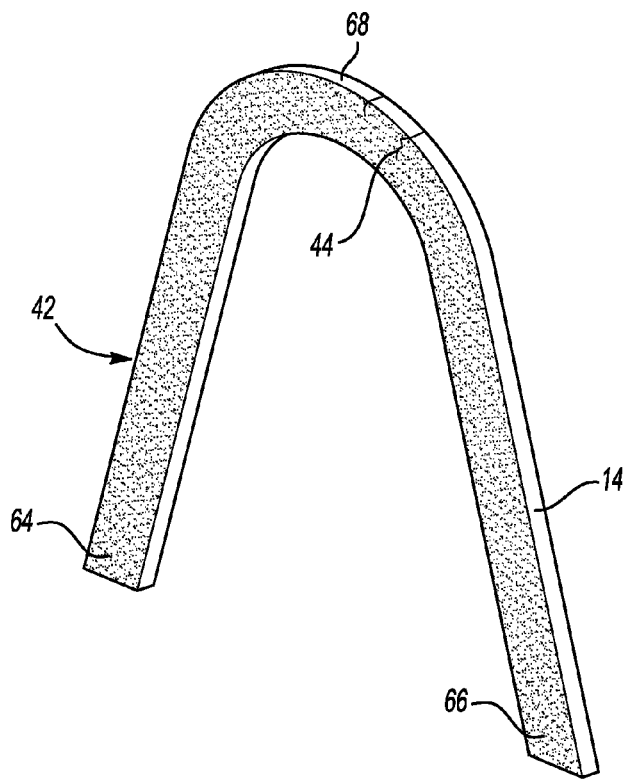
FIG. 6 is a perspective view of a test specimen after bending to simulate a stretch forming operation.

Referring to FIG. 6, a bent test sample 44 is shown with the first end portion 64 and second end portion 66 being bent toward the same direction. The sidewall 14 is shown to include a stretched sidewall 68 with a plurality of small fractures 44.

According to the method of testing metal for a stretch flanging operation, the sample 10 is shown to have two planar sides 12 and 40 that have a sidewall 14 that extends between the planar sides. The sides 12, 40 of the sample 10 are retained in a fixture 8, 48 with the side being confined either in the nesting slot 38 or by the first and second clamping elements 52 and 54. The sidewall 14 of the sample 10 is bent about a curved surface, such as the radius forming surface 28 or mandrel 50. In-plane bending of the strip 10 is performed with the strip either being retained in a nesting slot 38 or between the first and second clamping elements 52 and 54. Buckling of the sample 10 is restricted outside of the planar area defined by the nesting slot 38 or the first and second clamping elements 52, 54.

The samples 10 may be trimmed transversely across a coil of metal or longitudinally relative to the direction that the coil is rolled. The test specimens may be trimmed at a 45° angle or at another angle that corresponds to the orientation of the stretch formed flange in a production part. The test may be repeated for rolling, transverse and 45° test sample orientation to determine whether the sample orientation has any effect on the strip flanging test.

The stretched portion of the sidewall 40 may be marked with a grid or other evenly spaced marking to permit measurement of the deformation of the bent sample 42. After the bending operation, the distance between the elements of the grid or other markings may be measured for subsequent analytical calculations.

The test can be used as a production test in stamping plants where advanced high strength steels, dual phase steels or aluminum alloys may be used to perform production parts. The test can determine the properties of material samples to provide evidence of property deviations from material specifications or to test for material quality variations. By testing the material prior to running a production unsuitable material may be returned to a material supplier and more detailed specification may be developed to assure the performance of difficult to form material in stretch flanging operations. In product design and development, samples may be tested that are taken with different elongation orientations, such as rolling, transverse, 45° orientations, or the like. Panels may be oriented for optimal performance during die design so that splits in stretch flanging operations may be avoided even when forming difficult to flange trimmed surfaces.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A test machine for testing an elongated planar metal sample that has two planar sides and a sidewall extending between the planar sides for suitability for use in a flanging operation in which a flange is stretched while the flange is formed, the test machine comprising:
   a mandrel;
   a first clamping element engaging one planar side of the sample and a second clamping element engaging the other planar side of the sample, wherein the first and second clamping elements are a plurality of washers assembled to the mandrel that secure the sample to the mandrel, wherein the first and second clamping elements engage an intermediate portion of the sample that is secured with the sidewall against the mandrel; and
   a first bending member and a second bending member engage a first end portion and a second end portion of the sidewall of the sample on opposite ends of the intermediate portion of the sample to bend the sample about the mandrel, and wherein the sidewall between the first end portion and second end portion is stretched while the first and second bending members bend the sample.

2. The test machine of claim 1 wherein the mandrel is secured to a fixture that retains the mandrel in a fixed location while the first and second bending members bend the sample about the mandrel.

3. The test machine of claim 1 wherein the first and second bending members are clamps that are moved together reciprocally relative to the mandrel.

4. The test machine of claim 1 wherein the sample is cut from a quantity of material that is to be used in the flanging operation.

* * * * *